(12) United States Patent
Wang

(10) Patent No.: US 8,920,811 B2
(45) Date of Patent: Dec. 30, 2014

(54) RECOMBINANT ADENOVIRUS USEFUL FOR TREATING MALIGNANCY OVER-EXPRESSING PROTO-ONCOGENE NEU/ERB B2

(76) Inventor: Shangwu Wang, Guandong (CN)

( * ) Notice: Subject to any disclaimer, the term of this patent is extended or adjusted under 35 U.S.C. 154(b) by 316 days.

(21) Appl. No.: 12/450,632

(22) PCT Filed: Apr. 2, 2008

(86) PCT No.: PCT/CN2008/000663
§ 371 (c)(1),
(2), (4) Date: Oct. 2, 2009

(87) PCT Pub. No.: WO2008/119258
PCT Pub. Date: Oct. 9, 2008

(65) Prior Publication Data
US 2010/0221811 A1    Sep. 2, 2010

(30) Foreign Application Priority Data

Apr. 3, 2007   (CN) .......................... 2007 1 0027361

(51) Int. Cl.
| | | |
|---|---|---|
| *A61K 39/12* | (2006.01) | |
| *A61K 39/00* | (2006.01) | |
| *A61K 39/23* | (2006.01) | |
| *C07H 21/04* | (2006.01) | |
| *C12N 7/00* | (2006.01) | |
| *C12N 15/00* | (2006.01) | |
| *C07K 16/32* | (2006.01) | |
| *C07K 16/00* | (2006.01) | |
| *C12N 15/62* | (2006.01) | |
| *C12N 15/861* | (2006.01) | |
| *A61K 35/00* | (2006.01) | |
| *A61K 48/00* | (2006.01) | |

(52) U.S. Cl.
CPC ................. *C07K 16/32* (2013.01); *C12N 15/62* (2013.01); *C12N 15/861* (2013.01); *A61K 35/13* (2013.01); *A61K 48/00* (2013.01); *A61K 2039/505* (2013.01); *C07K 16/00* (2013.01); *C07K 16/005* (2013.01); *C07K 2317/565* (2013.01); *C12N 2799/022* (2013.01); *C12N 2799/04* (2013.01); *C12N 2830/36* (2013.01); *C12N 2840/203* (2013.01)
USPC ........................................................ 424/199.1

(58) Field of Classification Search
CPC .. A61K 2039/505; C07K 16/32; C12N 15/62; C12N 15/861; C12N 2799/022; C12N 2840/203
USPC .............. 424/192.1, 199.1, 233.1; 435/235.1, 435/320.1; 536/24.1, 24.2
See application file for complete search history.

(56) References Cited

PUBLICATIONS

Bocangel et al., 2006, Cancer Gene Therapy, vol. 13, p. 958-968.*
Arafat et al., 2002, Gene Therapy, vol. 9, p. 256-262.*
Adams et al., 1993, Cancer research, vol. 53, p. 4026-4034.*

* cited by examiner

*Primary Examiner* — Shin Lin Chen

(57) ABSTRACT

A recombinant adenovirus is applied for treating malignancy of over-expressing proto-oncogene neu/erbB2, wherein an expression cassette, which co-expresses the humanized monoclonal antibody variable region gene of anti proto-oncogene neu/erbB2 and the Mda-7/IL-24 gene, is inserted into E1 deletion region of the recombinant adenovirus. The recombinant adenovirus effectively treats the malignancy of overexpressing proto-oncogene neu/erbB2 without damaging normal cells, such that the recombinant adenovirus is able to be used for the gene therapy of malignancy tumors overexpressing proto-oncogene neu/erbB2.

1 Claim, 3 Drawing Sheets

SEQUENCE LISTING

```
<160> NUMBER OF SEQ ID NOS: 4

<210> SEQ ID NO 1
<211> LENGTH: 784
<212> TYPE: DNA
<213> ORGANISM: Artificial
<220> FEATURE:
<223> OTHER INFORMATION: Fused nucleotide sequence by light chain
      variable region and heavy chain variable region of the humanized
      antibody against proto-oncogene NEU/ERBB2 by a linker

<400> SEQUENCE: 1
gtaagcttgc tagcatgtac aggatgcaac tcctgtcttg cattgcacta agtcttgcac     60
ttgtcacaaa cagtgatatc cagatgaccc agtccccgag ctccctgtcc gcctctgtgg    120
gcgatagggt caccatcacc tgccgtgcca gtcaggatgt gaatactgct gtagcctggt    180
atcaacagaa accaggaaaa gctccgaaac tactgattta ctcggcatcc ttcctctact    240
ctggagtccc ttctcgcttc tctggctcaa gatctgggac ggatttcact ctgaccatca    300
gcagtctgca gccggaagac ttcgcaactt attactgtca gcaacattat actactcctc    360
ccacgttcgg acagggtacc aaggtggaga tcaaaggtgg cggtggctcg gaggttcagc    420
tggtggagtc tggcggtggc ctggtgcagc caggggggctc actccgtttg tcctgtgcag    480
cttctggctt caacattaaa gacacctata tacactgggt gcgtcaggcc ccgggtaagg    540
gcctgaaatg ggttgcaagg atttatccta cgaatggtta tactagatat gccgatagcg    600
tcaagggccg tttcactata agcgcagaca catccaaaaa cacagcctac ctgcagatga    660
acagcctgcg tgctgaggac actgccgtct attattgttc tagatgggga ggggacggct    720
tctatgctat ggactactgg ggtcaaggaa ccctggtcac cgtctcctcg taggcggccg    780
caga                                                                784
```

<210> SEQ ID NO 2
<211> LENGTH: 252
<212> TYPE: PRT
<213> ORGANISM: Artificial
<220> FEATURE:
<223> OTHER INFORMATION: Amino acid sequences for fused protein for variable region of humanized antibody against proto-oncogene NEU/ERBB2

<400> SEQUENCE: 2

Met Tyr Arg Met Gln Leu Leu Ser Cys Ile Ala Leu Ser Leu Ala Leu
1               5                   10                  15

Val Thr Asn Ser Asp Ile Gln Met Thr Gln Ser Pro Ser Ser Leu Ser
            20                  25                  30

Ala Ser Val Gly Asp Arg Val Thr Ile Thr Cys Arg Ala Ser Gln Asp
        35                  40                  45

Val Asn Thr Ala Val Ala Trp Tyr Gln Gln Lys Pro Gly Lys Ala Pro
    50                  55                  60

Lys Leu Leu Ile Tyr Ser Ala Ser Phe Leu Tyr Ser Gly Val Pro Ser
65                  70                  75                  80

Arg Phe Ser Gly Ser Arg Ser Gly Thr Asp Phe Thr Leu Thr Ile Ser
                85                  90                  95

Ser Leu Gln Pro Glu Asp Phe Ala Thr Tyr Tyr Cys Gln Gln His Tyr
            100                 105                 110

Thr Thr Pro Pro Thr Phe Gly Gln Gly Thr Lys Val Glu Ile Lys Gly
        115                 120                 125

Gly Gly Gly Ser Glu Val Gln Leu Val Glu Ser Gly Gly Gly Leu Val
    130                 135                 140

Gln Pro Gly Gly Ser Leu Arg Leu Ser Cys Ala Ala Ser Gly Phe Asn
145                 150                 155                 160

Ile Lys Asp Thr Tyr Ile His Trp Val Arg Gln Ala Pro Gly Lys Gly
                165                 170                 175

Leu Lys Trp Val Ala Arg Ile Tyr Pro Thr Asn Gly Tyr Thr Arg Tyr
            180                 185                 190

Ala Asp Ser Val Lys Gly Arg Phe Thr Ile Ser Ala Asp Thr Ser Lys
        195                 200                 205

Asn Thr Ala Tyr Leu Gln Met Asn Ser Leu Arg Ala Glu Asp Thr Ala
    210                 215                 220

Val Tyr Tyr Cys Ser Arg Trp Gly Gly Asp Gly Phe Tyr Ala Met Asp
225                 230                 235                 240

Tyr Trp Gly Gln Gly Thr Leu Val Thr Val Ser Ser
                245                 250

<210> SEQ ID NO 3
<211> LENGTH: 641
<212> TYPE: DNA
<213> ORGANISM: Homo sapiens

<400> SEQUENCE: 3
agcgggccca tgaattttca acagaggctg caaagcctgt ggactttagc cagacccttc      60
tgccctcctt tgctggcgac agcctctcaa atgcagatgg ttgtgctccc ttgcctgggt     120
tttaccctgc ttctctggag ccaggtatca ggggcccagg ccaagaatt ccactttggg      180 ccctgccaag tgaagggggt tgttccccag aaactgtggg aagccttctg ggctgtgaaa     240
gacactatgc aagctcagga taacatcacg agtgcccggc tgctgcagca ggaggttctg     300
cagaacgtct cggatgctga gagctgttac cttgtccaca ccctgctgga gttctacttg     360

```
aaaactgttt tcaaaaacta ccacaataga acagttgaag tcaggactct gaagtcattc    420
tctactctgg ccaacaactt tgttctcatc gtgtcacaac tgcaacccag tcaagaaaat    480
gagatgtttt ccatcagaga cagtgcacac aggcggtttc tgctattccg gagagcattc    540
aaacagttgg acgtagaagc agctctgacc aaagcccttg gggaagtgga cattcttctg    600
acctggatgc agaaattcta caagctctga ttctagagtc g                        641
```

<210> SEQ ID NO 4
<211> LENGTH: 206
<212> TYPE: PRT
<213> ORGANISM: Homo sapiens

<400> SEQUENCE: 4

```
Met Asn Phe Gln Gln Arg Leu Gln Ser Leu Trp Thr Leu Ala Arg Pro
1               5                   10                  15

Phe Cys Pro Pro Leu Leu Ala Thr Ala Ser Gln Met Gln Met Val Val
                20                  25                  30

Leu Pro Cys Leu Gly Phe Thr Leu Leu Leu Trp Ser Gln Val Ser Gly
            35                  40                  45

Ala Gln Gly Gln Glu Phe His Phe Gly Pro Cys Gln Val Lys Gly Val
        50                  55                  60

Val Pro Gln Lys Leu Trp Glu Ala Phe Trp Ala Val Lys Asp Thr Met
65                  70                  75                  80

Gln Ala Gln Asp Asn Ile Thr Ser Ala Arg Leu Leu Gln Gln Glu Val
                85                  90                  95

Leu Gln Asn Val Ser Asp Ala Glu Ser Cys Tyr Leu Val His Thr Leu
            100                 105                 110

Leu Glu Phe Tyr Leu Lys Thr Val Phe Lys Asn Tyr His Asn Arg Thr
        115                 120                 125

Val Glu Val Arg Thr Leu Lys Ser Phe Ser Thr Leu Ala Asn Asn Phe
    130                 135                 140

Val Leu Ile Val Ser Gln Leu Gln Pro Ser Gln Glu Asn Glu Met Phe
145                 150                 155                 160

Ser Ile Arg Asp Ser Ala His Arg Arg Phe Leu Leu Phe Arg Arg Ala
                165                 170                 175

Phe Lys Gln Leu Asp Val Glu Ala Ala Leu Thr Lys Ala Leu Gly Glu
            180                 185                 190

Val Asp Ile Leu Leu Thr Trp Met Gln Lys Phe Tyr Lys Leu
        195                 200                 205
```

RECOMBINANT ADENOVIRUS USEFUL FOR TREATING MALIGNANCY OVER-EXPRESSING PROTO-ONCOGENE NEU/ERB B2

BACKGROUND OF THE PRESENT INVENTION

1. Field of Invention

The present invention relates to a recombinant adenovirus, and more particularly to the recombinant adenovirus co-expressing the humanized monoclonal antibody variable region gene of anti proto-oncogene neu/erbB2 and the Mda-7/IL-24 gene.

2. Description of Related Arts

The researches show that the proto-oncogene neu/erbB2 is a main mark gene of many kinds of malignant tumors, which is also called malignant protein. The neu/erbB2 gene is in an over-expressing state in about 30% of the patients suffering breast cancer and in partial patients with other cancers, such as ovarian cancer, lung cancer, and gastric cancer, which is one of the main reasons that these tumors become malignant and metastasis.

Some countries have successfully developed the humanized monoclonal antibody against the proto-oncogene neu/erbB2. The humanized monoclonal antibody against the proto-oncogene neu/erbB2, which has been approved by FDA, exists in the current market and the clinical applications showing that the humanized monoclonal antibody can effectively treat the malignant breast cancer and has been clinically approved. (Carter P, et al: PNAS, 1992, 4285-4289; Stebbing. J., et al: Cancer Treat. Reviews 2000; 26:287-290). Although the humanized monoclonal antibody can effectively treat malignant breast cancer with over-expressing the proto-oncogene, the clinical researches show that a resistance to the antibody occurs within one year in most of the patients with metastatic breast cancer being effectively treated via the antibody, and 15% of the patients will have relapse. Therefore, combining other medicine or other therapies is the main objective for increasing the effectiveness of the antibody and overcoming the resistance to the antibody when treating breast cancer over expressing the neu/erbB2 by the antibody (Tseng P H, et al: Mol Pharmacol. 2006 November; 70(5): 1534-41; Nahta R, et al: Breast Cancer Res. 2006; 8(6): 215).

In addition, the researches also show that the application of variable region of the humanized monoclonal antibody not only has function of the antibody, but also increase penetration of the therapeutic antibody into tumors and its residence time in tumor tissue and blood. (Gregory P, et al: Cancer Research 1993, 53:4026-4034; Adams G P, et al: Brit. J Cancer (1998); 77(9): 1405-1412). The above built a firmly foundation for the drug treatment of single-chain variable region or Fab fragment of the monoclonal antibody.

Recently, the pegylated Fab fragment of tumor necrosis factor antibody has been proved due to its effectively control of the rheumatoid arthritis and chronic colitis, and approved by the United States FDA for the clinical applications, which show that monoclonal antibody single-chain variable region or Fab fragment used as a drug for treatment is practical.

In the recent years, the melanoma differentiation associated (mda) gene applied on clinical assessment, also called interleukin (IL-24), is one of the members of the interleukin-10 family. Mda-7/IL-24 gene is a conservative gene in structure. The expression product of the Mda-7/IL-24 gene is saddle-glycoprotein composed via 206 amino acids, wherein the saddle-glycoprotein is able to induce the interleukin-6, interferon-γ, tumor necrosis factor alpha, interleukin-1β, interleukin-12, and granulocyte macrophage colony-stimulating factor to express (Devanand Sarkar, et al: PNAS, 2005. 105(39): 14034-14039), so as to have multiple anti-tumor effect. Multiple tumor animal model experiments proof that the Mda-7/IL-24 has the ability of distinguish between normal cells and tumor cells, being able to induce the apoptosis function of the tumor cells, to inhibit the formation of tumor angiogenesis and tumor growth, to regulate immune responses, and to increase the sensitivity of tumor cell to chemical drugs, and biological agents, while has no significant poison effect on normal cells. So Mda-7/Il-24 is a specific tumor apoptosis factor having a cytokines of dual role, wherein the normal physiological function of Mda-7/IL-24 may be related to immune system, and the over expressing of the Mda-7/IL-24 may lead the apoptosis of specific tumor cells (Fisher P B, et al: Cancer Biol Ther. 2003 July-August; 2(4Suppl 1): S23-37; Fisher P B et al: Curr Gene Ther. 2006 February; 6(1): 73-91; Gupta P, et al: Pharmacol Ther. 2006 September; 111(3): 596-628. Epub 2006 Feb. 7). So far, the efficacy of clinical assessment is being satisfied. In the clinical assessment of advanced adenocarcinoma patients it is proved the safety and well tolerant. The intratumoral injection is able to kill the tumor cells via the cell apoptosis.

In some other countries, the clinical researches has confirmed treatment of the malignant breast cancer via the humanized monoclonal antibody combining with the Mda-7/IL-24 is more effective than using the humanized monoclonal antibody only, or combining with the chemotherapy, and may also kill the metastasized tumor cells (Bocangel D, et al: Cancer Gene Ther. 2006 October; 13(10): 958-68).

As the above mentioned researches and clinical assessments, to build a recombinant adenovirus co-expressing variable region gene of the humanized antibody and Mda-7/IL-24 gene for a more effective treatment of malignancy of overexpressing proto-oncogene neu/erbB2 is feasible.

SUMMARY OF THE PRESENT INVENTION

A main object of the present invention is to provide a recombinant adenovirus for treating malignancy of over-expressing proto-oncogene neu/erbB2, wherein the recombinant adenovirus co-expresses the humanized monoclonal antibody variable region gene of anti proto-oncogene neu/erbB2 and Mda-7/IL-24 gene.

Another object of the present invention is to provide a method for using the recombinant adenovirus.

Accordingly, in order to accomplish the above objects, the present invention provides a recombinant adenovirus for treating malignancy of overexpressing proto-oncogene neu/erbB2, wherein a E1 deletion region of the recombinant adenovirus is inserted into an expression cassette co-expressing a variable region gene of humanized monoclonal antibody of anti proto-oncogene neu/erbB2 and Mda-7/IL-24 gene, wherein the expression cassette comprises a promoter, the humanized monoclonal antibody variable region gene of anti proto-oncogene, internal ribosome entry site IRES fragment, Mda-7/IL-24 gene, and SV40 poly-adenine.

The expression cassette comprises the following characteristics.

(a) The variable region fusion gene described is from the humanized monoclonal antibody against the proto-oncogene neu/erbB2.

(b) Within the sequence of the variable region fusion gene of the humanized monoclonal antibody against the proto-oncogene neu/erbB2, light chain variable region and heavy chain variable region are bonding together through amino acid peptide -G-G-G-G-G-S-(GS1), wherein the N-terminal of the variable region fusion gene is bonded to lower stream of CMV promoter via endonuclease Nhe1 site, and the C-terminal of the humanized monoclonal antibody is bonded to upper stream of the IRES fragment via endonuclease Not 1 site.

(c) N-terminal of the Mda-7 gene is bonded to lower stream of the IRES fragment via endonuclease Sma1 site, and C-terminal of the Mda-7 gene is bonded to upper stream of the SV40 poly-adenine via endonuclease Xba1 site.

The expression cassette comprises the following amino acid sequences.

(a) An amino acid sequence of pro-polypeptide of the human Mda-7.

(b) The amino acid encoded by the variable region fusion gene of the humanized monoclonal antibody of the proto-oncogene neu/erbB2. An upper stream gene of the internal ribosome entry site is humanized monoclonal antibody variable region, wherein a lower stream gene of the internal ribosome entry site is Mda-7 gene, promoting cell apoptosis gene, or immune regulating factor. The promoting cell apoptosis gene is Noxa, p53RFP, or P27(Kip1), wherein the immune regulating factor is IL-2, IL-6, IFN-γ, granulocyte/macrophage colony-stimulating factor (GMCSF), or TNF-a.

The promoter is one or combination of two CMV promoter, virus promoter, or tumor-specific promoter. The tumor-specific promoter is one of or the combination of murine tumor-specific PEG-3 gene promoter, human telomerase promoter, estrogen and hypoxia response promoter, human prostate cancer-specific promoter, and alpha-fetoprotein promoter.

Preferably, the adenovirus vector used in the present invention is the AdEasy-1 vector of Stratagene company product, which is the vector of replication defective with deletion of E1 and E3 region. The present invention is not limited to use the replication defective Ad5 type adenovirus. The conditional replication adenovirus vectors may also be used in the present invention.

The recombinant adenovirus co-expressing the humanized monoclonal antibody variable region of proto-oncogene neu/erbB2 and the Mda-7 is used in a drug treatment of gene therapy for multiple malignancies of over-expressing proto-oncogene neu/erbB2. The effective anti cancer ingredients are the humanized monoclonal antibody variable region gene of proto-oncogene neu/erbB2 and an expressing protein of the Mda-7 gene.

The expressing structure of the recombinant adenovirus co-expressing the humanized monoclonal antibody variable region gene of proto-oncogene neu/erbB2 and the Mda-7/IL-24 has the following characteristics. (1). The antibody of anti neu/erbB2 proto-oncogene is the humanized monoclonal variable region. (2). N-terminal of the humanized monoclonal variable region is bonded with secreted peptide of 20 amino acids of N-terminal of IL-2. (3). Mda-7/IL-24 is a fragment of a full length gene formed via 206 amino acids. (4). The fragment of the humanized monoclonal antibody variable region gene is bonded with the Mda-7/IL-24 gene via the internal ribosome entry site IRES fragment. (5). The expression cassette co-expressing the Mda-7/IL-24 gene and the humanized monoclonal antibody variable region is formed by a promoter, the humanized monoclonal antibody variable region gene of anti proto-oncogene, internal ribosome entry site IRES fragment, Mda-7/IL-24 gene, and SV40 poly-adenine. Therefore, the recombinant adenovirus of the present invention co-expresses the Mda-7/IL-24 gene and the humanized monoclonal antibody variable region, so as to increase the ability of cell apoptosis.

These and other objectives, features, and advantages of the present invention will become apparent from the following detailed description, the accompanying drawings, and the appended claims.

BRIEF DESCRIPTION OF THE DRAWINGS

FIG. 3 is for cloning of Mda-7 gene and analysis for electrophoresis of endonuclease digestion according to the preferred embodiment of the present invention. After the RT-PCR reaction, the Mda-7 gene is cloned at the T-Easy vector, and T-Easy-Mda-7 plasmid DNA is digested with EcoR1 endonuclease. And the first column is λ DNA/HindIII DNA molecular markers, the second column is 100bp-ladder DNA molecular marker, and the third column is for the Mda-7 gene cut with EcoR1 endonuclease, producing two fragments as the arrows point to.

DETAILED DESCRIPTION OF THE PREFERRED EMBODIMENT

Figure 1:
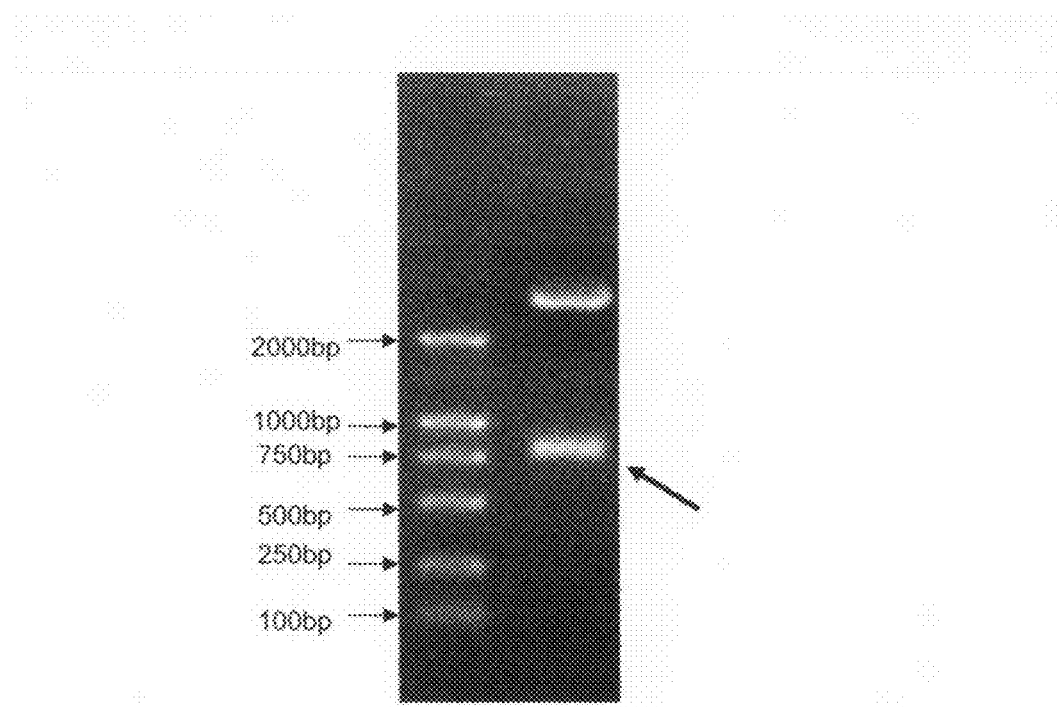
FIG. 1 is humanized monoclonal antibody scFv fusion gene of proto-oncogene neu/erbB2 according to a preferred embodiment of the present invention, wherein a first column is DNA molecular marker, and the second column is the cleaving result of plasmid containing the scFv fusion gene by endonuclease EcoR1, and the arrow pointing to is a fragment of the scFv fusion gene encoding humanized monoclonal antibody of proto-oncogene neu/erbB2.
Figure 2:
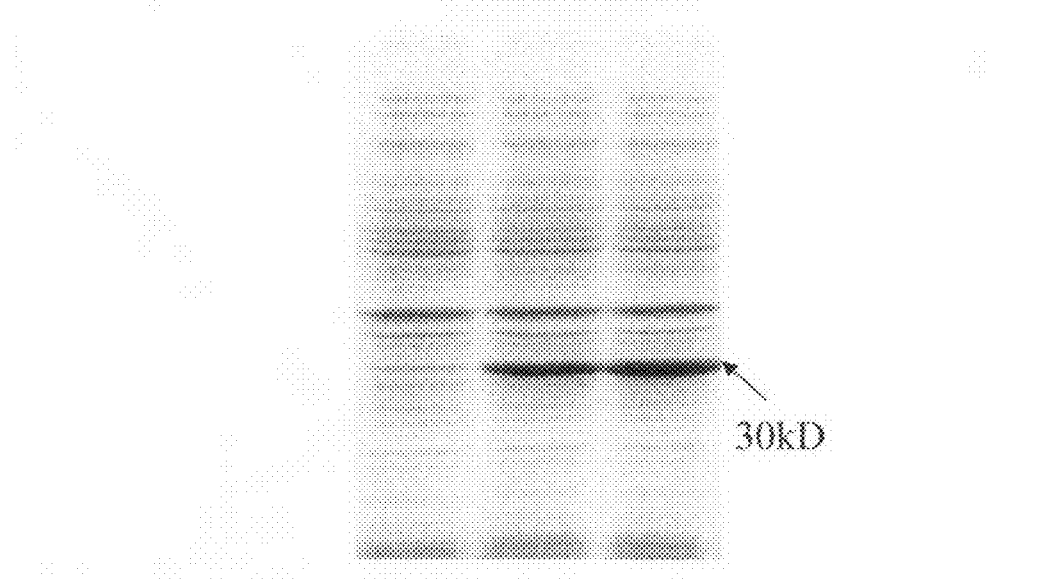
FIG. 2 is the SDS-PAGE gel analysis according to the preferred embodiment of the present invention, wherein a first column is an uninduced bacterial total protein, and a second column and third column are one hour and three hours induced bacterial total protein respectively, wherein the arrow pointed line is the expressing product of the scFv.
Figure 3:
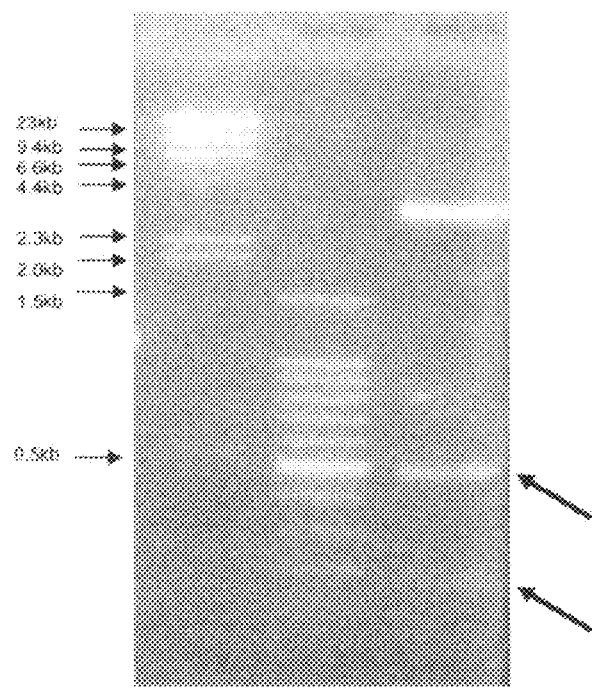
Figure 4:
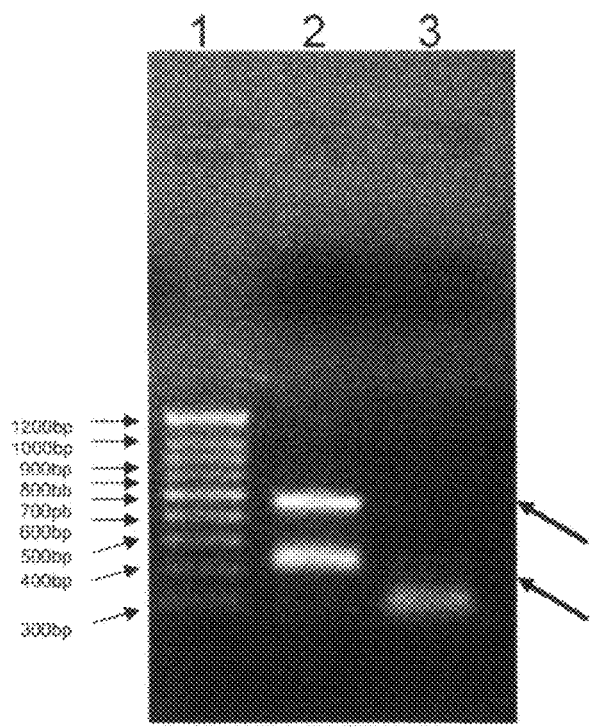
FIG. 4 is a RT-PCT analysis of expressing plasmid pShuttle-scFv-IRES-Mda-7 after transfecting Hela cells according to the preferred embodiment of the present invention, wherein the first column is 100 bp ladder DNA molecular marker, the second column is for RT-PCR products of both scFv fusion gene encoding neu/erbB2 humanized monoclonal antibody as pointed by the up-arrow and Mda-7 gene as pointed by the low-arrow. And the third column is for control group of Hela cells untransfected.
Figure 5:
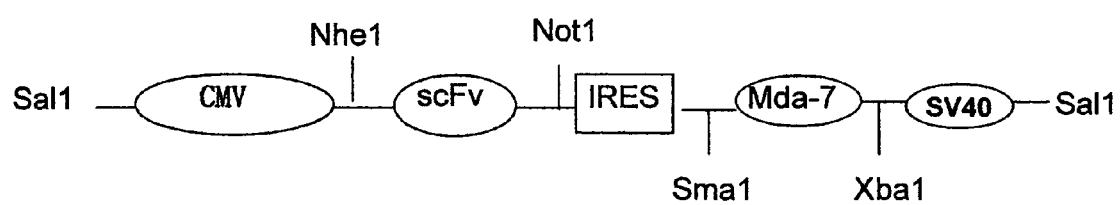
FIG. 5 is an illustrative plate of expression cassette driven by the CMV promoter according to the preferred embodiment of the present, illustrating the expression cassette is formed via CMV promoter at the N-terminal of the expression cassette, the humanized monoclonal antibody scFv of proto-oncogene, IRES, Mda-7, and SV40 poly-adenine, which are introduced into the expression cassette via variety of endonuclease and the sites thereof.
Figure 6:
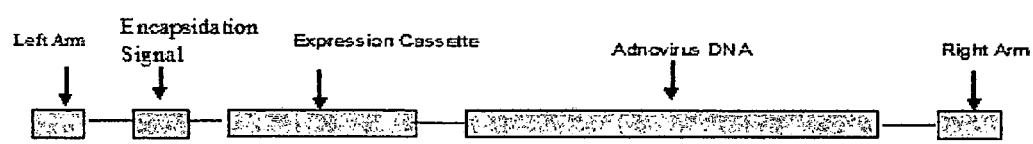
FIG. 6 is a structure of the recombinant adenovirus co-expressing a humanized monoclonal antibody scFv fusion gene of anti proto-oncogene neu/erbB2 and Mda-7/IL-24 according to the preferred embodiment of the present invention, wherein two ends of the structure are right arm and left arm of the adenovirus respectively, wherein the expression cassette is formed by the CMV promoter, internal ribosome entry site (IRES), Mda-7 gene, and SV40 poly-adenine.

One skilled in the art will understand that the embodiment of the present invention as shown in the drawings and described above is exemplary only and not intended to be limited. The adenovirus vector used in the present invention is the product of the Stratagene company, wherein the products includes adenovirus vector pAdeasy-1, plasmid pShuttle, and pShuttle-IRES.

A first preferred embodiment of the present invention illustrates a recombinant adenovirus for treating malignancy of over-Expressing proto-oncogene neu/erbB2.

The process of construct of humanized monoclonal antibody of proto-oncogene neu/erbB2 (including a bonding between a light chain variable region and heavy chain variable region of humanized monoclonal antibody, and including expression plasmid of scFv gene) comprises the steps of followings.

(1) The bonding between the light chain and heavy chain of humanized monoclonal antibody variable region:

(a) Firstly use a cDNA of the humanized monoclonal antibody as replication template, and synthetic primers for PCR reaction to amplify the variable region of light chain of the humanized monoclonal antibody to introduce endonuclease sites of Hind111 and Nhe1 and a signal peptide of interleukin-2 (IL-2) formed by 20 amino acids into N-terminal of the light chain variable region, wherein a C-terminal of the light chain has the endonuclease Kpn1 site. This is done by twice PCR reactions, that is, the first PCR reaction is done by using primer 2 and primer 3, and then the second PCR reaction is done by using the product of the first PCR reaction as a template and primer 1 and 3.

The PCR primers are designed as follows:

```
The primer 1:
5'-gtaagcttgctagcatgtacaggatgcaactcctgtcttgcattgca ctaagtcttgcattgt-3'

The primer 2:
5'-actaagtccttgcacttgtcacaaacagtgatatccagatgaccc a-3'

The primer 3:
5'-agctgaacctcacttttgatctccaccttggtaccctgtccg-3'
```

The PCR product is purified and ligated with T-easy vector after added a poly-adenine (A Tailing reaction), and then transformed into competent cells. After the transformation of competent cells, T-easy plasmid is extracted from cultured competent cells, and confirmed by digestion of endonuclease EcoR1, and DNA sequencing.

(b) Likewise, PCR is done to amplify the heavy chain variable region of the humanized monoclonal antibody and to add a sequence to N-terminal of the heavy chain variable region, which is composed of a endonuclease Kpn1 site, a linker composed of -G-G-G-G-S- and a sequences as same as that of C-terminal of light chain variable region, wherein the C-terminal the heavy chain variable region is added a Not1 endonuclease site.

The PCR primer is designed as follows:

```
Primer 4:
5'-acagggtaccaaggtggagatcaaaggtggcggtggctcggaggttc agctgg-3'

Primer 5:
5'-ctagcggccgccctacgaggagacggtgaccagggtt-3'
```

The PCR product is purified and added a poly-adenine (A Tailing reaction), then ligated to T-easy vector, and then transformed competent cells. After the transformation and culture of competent cells, the T-easy plasmid is extracted and purified, and then confirmed by DNA sequencing.

(c) The connection between the light chain variable region and heavy chain variable region of humanized monoclonal antibody: the endonuclease Nhe1 and Kpn1 are used to digest the above (a) T-easy vector, and endonuclease Kpn1 and Not1 are used to digest the above (b) T-easy vector, respectively, and then separate and purify the Nhe1-Kpn1 fragment of light chain variable region, and Kpn1-Not1 fragment of heavy chain variable region from 0.8% agarose, then ligate the both of the fragments described as above of the antibody, and then transform the competent cells. After all, extract the plasmid DNA, and then sequence it.

(2) After sequencing to confirm, use the endonuclease Nhe1 and Not1 digest the above T-easy vector of scFv to obtain a Nhe1-Not1 fragment comprised of the light chain variable region and heavy chain variable region of the antibody, and then purify the fragments. The fragments are further connected to the expression plasmid pET-45b, which had been pre-digested and pre-purified, to form an expression plasmid, pET-45b-scFv, having the humanized monoclonal antibody variable region scFv. Finally, after the transform competent cells and plasmid extracted, sequence and enzyme digest to confirm the above products.

A second preferred embodiment of the present invention illustrates a recombinant adenovirus for treating malignancy of over-Expressing proto-oncogene neu/erbB2:

Synthesize Mda-7 DNA fragment and its cloning.

According to a known gene sequence, the DNA sequence fragment of Mda-7 is synthesized via conventional way commonly known by one skilled in the art, wherein at the 5'-terminal of the Mda-7 adds a Sma1 1, and at the 3'-terminal of the Mda-7 adds a Xba 1 site, wherein the Mda-7 gene is amplified via PCR reaction.

```
Primer 1:
5'-agcgggccctatgaattttcaacagaggctgcaaagcctgtgg-3'

Primer 2:
5'-cgacagatctatcagagcttgtagaatttctgcatcc-3'
```

The PCR product is added a poly-adenine (A Tailing reaction), then ligated to T-easy vector, and then transformed into competent cells. After the transformation of competent cells and its culture, extract the T-easy plasmid, and then sequencing.

A third preferred embodiment of the present invention illustrates a recombinant adenovirus for treating malignancy of over-Expressing proto-oncogene neu/erbB2, wherein an expression cassette is formed by a CMV promoter, scFv, internal ribosome entry site IRES, and Mda-7.

Adapt a pShuttle-IRES vector, which is preferably a product of Stratagene Company, as a framework of construction of expression cassette. The construction of expression cassette is completed via several rounds of enzyme digesting, conjugating or connecting reactions, transforming of competent cells, and sequencing. In other words, the scFv fragments of the 5'-terminal Nhe1 and 3'-terminal Not1 endonuclease sites are connected to the upstream of the IRES; the Mda-7 gene fragments of the 5'-terminal Sma1 and 3'-terminal Xba1 endonuclease sites are connected to the upstream of the SV40 poly-adenine, so as to locate at the downstream of the IRES. Therefore, the expression cassette is completed.

A fourth preferred embodiment of the present invention illustrates a recombinant adenovirus for treating malignancy of over-Expressing proto-oncogene neu/erbB2 to construct an adenovirus plasmid comprising the above expression cassette.

(1) An endonuclease Sal1 is adapted for digesting the above pIRES plasmid DNA of the above expression cassette, and the digesting reaction generate a product of a DNA fragment of Sal1. Therefore, the expression cassette comprises the entire above expression cassette and the DNA sequences of SV 40 poly-adenine. After the digestion, separate the fragments via 1.2% agarose electrophoresis, and purify the needed DNA fragments for later use.

(2) Digest the pShuttle shuttle vector plasmid DNA, then electrophoresis the digested products via 1.2% agarose, and then purify the linearized pShuttle vector DNA for later use.

(3) A ligase enzyme is adapted for the ligation reaction of the linearized pShuttle vector DNA fragment and the Sal1 DNA fragment from the digested expression cassette, and then transforms the competent cells thereto and incubates it to amplify.

(4) Screen a bacterial transformants, incubate to expand it, and then extract the recombinant plasmid DNA. Finally, confirm the structures via enzyme digesting and DNA sequencing.

A fifth preferred embodiment of the present invention illustrates a recombinant adenovirus for treating malignancy of over-Expressing proto-oncogene neu/erbB2: recombinant adenovirus co-expressing the scFv and Mda-7 gene.

(1) Prepare a linearized recombinant shuttle plasmid pShuttle-scFv-Mda-7 comprising the scFv and the Mda-7 gene. Take a predetermined amount of the recombinant shuttle plasmid DNA, then digest it to completion via nucleotide endonuclease Pme1, and then electrophoreses it, purify the linearized recombinant shuttle plasmid DNA for later use.

(2) Homologous recombination. BJ5183-AD-1 bacterial, which was pre-transformed with adenovirus vector pAdEasy-1, is electroporated with above linearized recombinant shuttle plasmid DNA to perform homologous recombination, and then screen it on LB plate containing kamamycin antibiotics. The bacterial comprising the recombinant of adenovirus vector pAdEasy-1 is kamamycin$^R$ strain.

(3) Expand the recombinant of adenovirus vector pAdEasy-1, the kamamycin$^R$ strain, which is to expand the DNA of recombinant adenovirus vector pAdEasy-1. Extract the DNA of recombinant adenovirus vector pAdEasy-1, then digest the recombinant DNA to completion with endonuclease Pac1 to linearize the recombinant adenovirus vector pAdEasy-1, and then purify and separate it for later use.

(4) Transfect the above purified recombinant DNA of linearized adenovirus vector pAdEasy-1 into AD-embryonic kidney 293 cells in accordance with the manual of the product of AdEasy XL Adenoviral Vector System of Stratagene company.

(5) After 7-10 days of transfection of the AD-embryonic kidney 293 cells, prepare the original generation of recombinant adenovirus liquor and optimize the transfection condition of AD-embryonic kidney 293 cells of the original generation of recombinant adenovirus liquor to expand the recombinant adenovirus.

(6) Duplicate enough amount of high titer recombinant adenovirus for using in animals and researches.

It will thus be seen that the objects of the present invention have been fully and effectively accomplished. The embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A recombinant adenovirus for treating malignancy of over-expressing proto-oncogene Neu/erb B2, comprising an expression cassette consisting of a promoter, a fused gene, an internal ribosome entry site (IRES) fragment, a Mda-7/IL-24 gene and a SV40 poly adenine fragment, wherein said expression cassette is inserted in E1 deletion region of said recombinant adenovirus, and wherein said expression cassette comprises the characteristics of that as following:

(a) A DNA fragment coding a signal peptide of interleukin-2 (IL-2) formed by 20 amino acids is fused into the 5'-terminal of said fused gene;

(b) Said fused gene is composed of the nucleotide sequences encoding the light chain variable region peptide and the heavy chain variable region peptide of humanized monoclonal antibody against proto-oncogene neu/erb B2;

(c) The encoded peptide of the light chain variable region is fused to the encoded peptide of the heavy chain variable region by a linker composed of amino acid: -Gly-Gly-Gly-Gly-Gly-Ser-;

(d) Within said expression cassette, N-terminal of said fused gene is ligated to downstream of CMV promoter via endonuclease Nhe1 site and its C-terminal is ligated to upstream of the IRES fragment via endonuclease Not1 site;

(e) Within said expression cassette, N-terminal of Mda-7/IL-24 is ligated to downstream of IRES fragment via endonuclease Sma1 site and its C-terminal is ligated to upstream of SV40 poly adenine via endonuclease Xba1 site.

* * * * *